United States Patent [19]

Kamada

[11] Patent Number: 5,505,983
[45] Date of Patent: Apr. 9, 1996

[54] SPHERICAL SEED CORES, SPHERICAL GRANULES AND PROCESS FOR PRODUCTION THEREOF

[75] Inventor: Etsuo Kamada, Nobeoka, Japan

[73] Assignee: Asahi Kasei Kogyo Kabushiki Kaisha, Osaka, Japan

[21] Appl. No.: 325,952

[22] Filed: Oct. 17, 1994

Related U.S. Application Data

[62] Division of Ser. No. 3,661, Jan. 12, 1993, Pat. No. 5,384,130, which is a continuation of Ser. No. 686,481, Apr. 17, 1991, abandoned.

[30] Foreign Application Priority Data

Apr. 18, 1990 [JP] Japan ................... 2-100251

[51] Int. Cl.$^6$ .................... A61K 47/38; A61K 9/14; B05D 1/34
[52] U.S. Cl. .................. 427/2.21; 427/2.16; 427/2.19; 427/196; 427/214
[58] Field of Search .................. 427/2.16, 2.18, 427/2.19, 2.21, 196, 214, 426

[56] References Cited

U.S. PATENT DOCUMENTS

| | | |
|---|---|---|
| 3,146,168 | 8/1964 | Battista et al. . |
| 3,539,380 | 11/1970 | Johnson et al. . |
| 3,873,694 | 3/1975 | Kanig . |
| 4,159,345 | 6/1979 | Takeo et al. . |
| 4,176,175 | 11/1979 | Maekawa et al. ............ 427/2.18 |
| 4,261,971 | 4/1981 | Appelgren et al. ............ 424/21 |
| 4,274,830 | 6/1981 | Woznicki et al. ............ 427/2.2 |
| 4,302,440 | 8/1986 | John et al. ............ 427/2.18 |
| 4,489,026 | 12/1984 | Yalkowsky ............ 427/2.18 |
| 4,540,602 | 9/1985 | Motoyama et al. ............ 427/2.16 |
| 4,623,588 | 11/1986 | Nuwayser et al. ............ 427/2.16 |
| 4,684,534 | 8/1987 | Valentine ............ 427/2.16 |
| 4,744,987 | 5/1988 | Mehra et al. ............ 106/163.1 |
| 4,867,985 | 9/1989 | Heafield et al. . |
| 4,900,558 | 2/1990 | Barry et al. . |
| 4,917,900 | 4/1990 | Jones et al. ............ 424/493 |
| 5,026,560 | 6/1991 | Makino et al. . |
| 5,112,621 | 5/1992 | Stevens et al. ............ 427/2.16 |
| 5,188,836 | 2/1993 | Muhammad et al. ............ 424/431 |

FOREIGN PATENT DOCUMENTS

| | | |
|---|---|---|
| 0164967 | 12/1985 | European Pat. Off. . |
| 0277741 | 8/1988 | European Pat. Off. . |
| 61-213201 | 9/1986 | Japan . |

OTHER PUBLICATIONS

European Search Report, EP 91 10 5993, Jan. 5, 1993.
Patent Abstracts of Japan, vol. 11, No. 47 (C–403) (2494), published Feb. 13, 1987.

*Primary Examiner*—Diana Dudash
*Attorney, Agent, or Firm*—Finnegan, Henderson, Farabow, Garrett & Dunner

[57] ABSTRACT

Pharmacologically inactive spherical seed cores comprising at least 50% by weight of microcrystalline cellulose having an average degree of polymerization of 60 to 375, wherein the spherical seed cores have an average particle size of 100 to 1000 μm, a tapped bulk density of at least 0.65 g/ml, an aspect ratio of at least 0.7, a water absorption capacity of 0.5 to 1.5 ml/g, and a friability of no more than 1%; spherical granules comprising the spherical seed cores coated with a powdery layer comprising active ingredients and having an outer layer of coating provided on the powdery layer; and a process for the production of spherical granules, comprising the steps of coating the spherical seed cores with powder comprising active ingredients using an aqueous binding solution, spraying an aqueous solution or suspension of a coating agent thereon, and drying the resulting coated granules.

5 Claims, 1 Drawing Sheet

SPHERICAL SEED CORES, SPHERICAL GRANULES AND PROCESS FOR PRODUCTION THEREOF

This is a division of application Ser. No. 08/003,661, filed on Jan. 12, 1993, now U.S. Pat. No. 5,384,130, which was a continuation of application Ser. No. 07/686,481, filed Apr. 17, 1991, abandoned.

BACKGROUND OF THE INVENTION

1. Field of the Invention

The present invention relates to spherical seed cores, spherical granules comprising said seed cores and a process for production thereof.

2. Description of the Related Art

In many cases a pharmaceutical preparation is film-coated as a means for control of the delivery of sustained release-pharmaceuticals, for entero-solubilization, and for an improvement of the stability of active ingredients or a masking of the taste thereof. Where granules are film-coated, spherical elementary granules having a uniform particle size are often used, to enhance the yield and to improve the reproducibility of the coating. To produce spherical elementary granules having a uniform particle size, two main approaches are known. The first approach involves a method wherein a mixture of active ingredients and an excipient is kneaded and extruded to form spheres, as disclosed in Japanese Unexamined Patent Publication (Kokai) No. 63-227518. The second approach involves a method wherein spherical seed cores having a generally uniform particle size are coated with active ingredients and an excipient. In the former method, however, it is difficult to obtain small spherical granules having a particle size of not more than 500 μm, and the particle size distribution is broad and the aspect ratio thereof is unsatisfactory.

Therefore, where precise control of the dissolution rate of an active ingredient is desired, the latter method which provides spherical elementary granules having a uniform particle size is often used. In this case, Nonpareil (component: sucrose, or sucrose/starch) is often used as a seed core, as disclosed in Japanese Unexamined Patent Publication (Kokai) No. 61-1614.

Japanese Unexamined Patent Publication (Kokai) No. 61-213201 refers to microcrystalline cellulose spherical granules, which can be used as seed cores for coating, and having a bulk density of at least 0.65 g/ml and an aspect ratio of at least 0.8. Although this publication defines the aspect ratio as a ratio of the length of the short axis to the length of the long axis, it is not clear whether this aspect ratio relates to that of a particular granule or the average of all of the granules.

Japanese Unexamined Patent Publication (Kokai) No. 63-301816 describes and exemplifies the use of spherical seed cores made from microcrystalline cellulose. However, it does not define any characteristics of the seed cores except for a particle distribution range thereof of between 20 and 32 meshes, and does not describe microcrystalline cellulose as a starting material.

These publications do not disclose a water absorption capacity, and do not disclose the friability of the seed cores. There are believed to be important properties for spherical seed cores. Moreover, these publications do not refer to a process for the production of spherical granules comprising coating spherical seed cores with powder containing an active ingredient, using an aqueous binder solution, and spraying an aqueous solution or suspension of a coating agent thereon followed by drying.

In many cases where seed cores are coated with powder containing active ingredients, an organic or aqueous solution of a binder is used as a binder solution. When a coating is applied, a solution of a coating agent in an organic solvent is used. The use of an organic solvent brings problems relating to environmental pollution, cost, residues and the like. Thus, these organic solvents will be gradually replaced by aqueous solutions or suspensions.

Nevertheless, in a process for the preparation of a pharmaceutical wherein seed cores composed of sucrose or sucrose/starch are coated with a powder containing an active ingredient, using a binder aqueous solution, and further coated by spraying an aqueous solution or suspension of a coating agent, certain problems arise. For example, sucrose, which is a main ingredient of the seed cores, is dissolved, the surface of the seed cores becomes tacky, and the seed cores exhibit a high friability. These problems cause disadvantages, such as aggregation of granules, adhesion of granules to a wall of a coating machine, and a lowered yield. Moreover, the resulting granules have a problem in that the dissolution rate of the active ingredient from the granules is lowered with the passage of time. Further, upon administration, since sucrose, a main ingredient of the seed cores, is gradually dissolved. This results in a reduction of the strength of the granules. An intestinal movement may therefore break the coating of the granules. Since this coating is intended to control the dissolution of the active ingredient, a highly undesirable dissolution profile may appear.

SUMMARY OF THE INVENTION

The present inventor surprisingly found that the various above-mentioned problems can be resolved by providing pharmacologically inactive spherical seed cores containing at least 50% of microcrystalline cellulose having an average degree of polymerization of between 60 and 375.

Accordingly, the present invention provides pharmacologically inactive spherical seed cores comprising at least 50% of microcrystalline cellulose having an average degree of polymerization of between 60 and 375. The present invention also provides spherical granules comprising the spherical seed cores having a powder layer comprising a pharmacologically active ingredient and an outer film coating layer.

Moreover, the present invention provides a process for the production of the spherical granules, comprising the steps of coating the spherical seed cores with powder comprising a pharmacologically active ingredient, while using an aqueous binder solution, and spraying an aqueous solution or suspension of a coating agent to form spherical granules, and drying the spherical granules.

Since the present spherical seed cores have a high strength and are rarely disintegrated, when the spherical granules prepared from the spherical seed cores are administered in vivo, they are not destroyed by intestinal movement. Therefore, the coating layer of the granules is not broken and a desired profile is obtained.

The present invention uses pharmacologically inactive spherical seed cores containing at least 50% of microcrystalline cellulose having an average degree of polymerization of between 60 and 375, and an appropriate water absorption capacity. As a result, the aggregation of granules is as low as one tenth that of conventional granules and adhesion of the granules to a wall of a coating machine is prevented.

Therefore, precise control of production conditions such as the coating speed is not necessary, and high speed coating is possible. Moreover, since the friability is very low when coating, the yield is high. In addition, since the seed cores of the present spherical granules are substantially insoluble, the pharmacologically active ingredients are dissolved at a constant rate.

DESCRIPTION OF THE PREFERRED EMBODIMENTS

Figure 1:
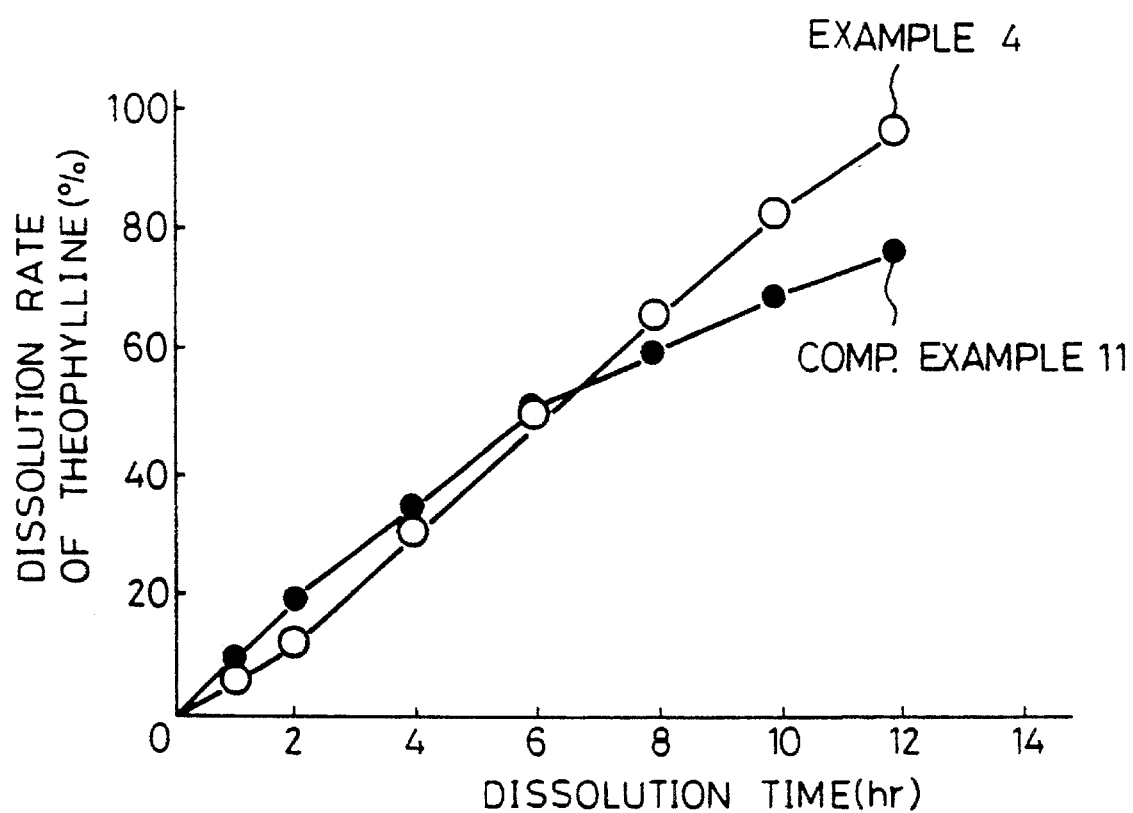
FIG. 1 is a graph comparing the dissolution rate of a pharmacologically active ingredient, i.e., theophylline of the spherical granules of the present invention (Example 4) granules (comparative Example 11).

The spherical seed cores of the present invention comprise microcrystalline cellulose having an average degree of polymerization of between 60 and 375, in an amount of at least 50% by weight of the whole seed cores, and are pharmacologically inactive. The phrase "pharmacologically inactive" as used herein means that the seed cores do not contain a pharmacologically active ingredient. The seed cores preferably have a water absorption capacity of 0.5 to 1.5 ml/g; an average particle size of 100 to 1000 μm, preferably 150 to 700 μm, more preferably 200 to 700 μm, an aspect ratio of at least 0.7, preferably at least 0.8; a tapped bulk density of at least 0.65 g/ml; and friability of not more than 1%; and are substantially not disintegrated in water.

Because they contain at least 50% by weight microcrystalline cellulose, the seed cores of the present invention are relatively easily formed into spheres, the strength of the resulting seed cores is high and they are substantially not disintegrated in water. In particular, the seed cores containing at least 80% of microcrystalline cellulose are preferred. More preferably, the seed cores are comprised of 100% by weight microcrystalline cellulose. This permits easy formulation of an excipient. If the microcrystalline cellulose content of the seed cores is less than 50% by weight, the formation of spherical particles is difficult and the strength of the seed cores is low.

If the water absorption capacity is less than 0.5 ml/g, then when an aqueous solution or suspension is sprayed on the granules, aggregation of granules and adhesion of granules to the walls of a machine increases. If the water absorption capacity is more than 1.5 ml/g, the amount of solution or suspension which is absorbed in the seed cores increases. Therefore, the yield of the powder is reduced.

If the aspect ratio of seed cores is less than 0.7, then the aspect ratio of spherical granules prepared from the seed cores is lower. Therefore, the spherical granules are disadvantageous in that they have a poor appearance and provide poor control of the pharmacologically active ingredient dissolution rate. Preferably, the aspect ratio is at least 0.8. The average particle size of the seed cores depends on the amount of powder containing pharmacologically active ingredients, the amount of coating and the particle size of the desired spherical granules. If the particle size of the seed cores is less than 100 μm, the coating operation becomes difficult and results in an increase in aggregation of granules. If it is more than 1000 μm, the amount of pharmacologically active ingredients to be coated is limited. It is preferably 150 to 700 μm, and more preferably 200 to 700 μm.

The tapped bulk density must be at least 0.65 g/ml. If it is lower, the flowability of the seed cores is low during the coating process. This results in difficulty in obtaining a uniform coating, and in increased aggregation of the granules. The friability of the spherical seed cores should be no more than 1%. If it is more than 1%, the yield is decreased. These spherical seed cores substantially have a sufficient strength such that they are not disintegrated in water. Therefore, when administered in vivo, the granules are maintained without disintegration until dissolution of pharmacologically active ingredients is completed, and thus a desired dissolution profile is obtained. Moreover, the amount of soluble ingredients is very low compared with conventional seed cores comprising sucrose. Therefore, it does not affect the dissolution of pharmacologically active ingredients, and thus an easy dissolution control is obtained.

The microcrystalline cellulose used in the present invention is a product obtained by acidolysis or alkaline oxidation or a combination thereof of a cellulosic material such as linters, pulp, regenerated fiber or the like, or a product obtained by mechanical treatment such as grinding of the above-mentioned chemically treated product. The microcrystalline cellulose should have an average degree of polymerization of 60 to 375, and preferably 60 to 300. The term microcrystalline cellulose as used herein means cellulose having a crystallinity of at least 10%, and preferably at least 40%, as determined by X-ray diffractometry. Preferably, the microcrystalline cellulose has a water absorption capacity of 1.0 to 2.8 ml/g, and no more than 80% of its fractions is retained on a 200 mesh-sieve. A lower average degree of polymerization provides poor entanglement of the cellulose molecules, resulting in higher friability of the spherical seed cores. An average degree of polymerization of more than 375 provides fibrous properties which cause difficulties in sphere-formation.

In addition to microcrystalline cellulose, the present spherical seed cores may contain sugars such as lactose, sucrose or D-mannitol; starch such as corn starch or potato starch; or an inorganic substance such as dibasic calcium phosphate or aluminium silicate, or a combination thereof.

The spherical seed cores of the present invention can be prepared, for example, by the following process, but the invention is not limited thereto. A powder containing at least 50% by weight microcrystalline cellulose is kneaded with distilled water in a mixing granulator. An aqueous solution of hydroxypropyl cellulose, starch paste, polyvinyl pyrrolidone or the like can be used in place of the distilled water. Next, the kneaded mixture is transferred to a rotating type coating machine, and is subjected to sphere-formation while spraying with water. The spheres are then dried, and sieved, if necessary to obtain spherical seed cores.

Spherical granules can be prepared as follows. While rotating the spherical seed cores in a centrifugal fluidized type corting machine, an aqueous binder solution is sprayed thereon. Simultaneously a powder containing a pharmacologically active ingredient and, if necessary, an excipient is fed thereto to coat the spherical seed cores with the powder to form elementary granules. Alternatively, while fluidizing spherical seed cores in a fluidized bed coating apparatus, an aqueous binder solution in which a pharmacologically active ingredient is dissolved or suspended is sprayed thereon, to coat the spherical seed cores with powder containing a pharmacologically active ingredient and form elementary granules. If necessary, the elementary granules are dried. Then an aqueous solution or suspension of a coating agent is sprayed thereon and the coated granules are dried to form a coating layer, thereby forming spherical granules. The coating is intended, to inter alia, be moisture-proof, capable of masking any bitter taste, permit enteric dissolution, or sustained release, and the like. Alternatively, when the spherical seed cores are coated with powder containing a pharmacologically active ingredient, an aqueous solution or suspension of a coating agent may be simultaneously sprayed thereon.

The amount of powder to be coated depends on the amount of pharmacologically active ingredient to be administered, the size of the final granules, and the like, and is preferably 5 to 300% by weight or more of the spherical seed cores. Although any pharmacologically active ingredients can be used in the present invention, the advantages of the present invention are clearer when using water soluble pharmacologically active ingredients, because if such pharmacologically active ingredients are dissolved in an aqueous binder solution, the surface of granules becomes tacky and the resulting granules are easily aggregated.

Suitable binding agents include hydroxypropyl cellulose (HPC), hydroxypropylmethyl cellulose (HPMC), methyl cellulose, starch paste, pregelatinized starch, polyvinyl pyrrolidone, gum arabic, sugar syrup, sodium carboxymethyl cellulose, and the like. When the pharmacologically active ingredient is water soluble, an aqueous solution of the pharmacologically active ingredient may be used as a binder solution.

Suitably excipients include lactose, corn starch (CS), microcrystalline cellulose (MCC), sucrose, p-mannitol, pregelatinized starch, partly pregelatinized starch and the like.

As the coating machine, a centrifuged fluidized type coating machine, fluidized bed coating machine, fluidized bed coating machine with rotating equipment, pan type coating machine or the like may be used.

Suitable examples of the aqueous solution of the coating agent include an aqueous solution of HPMC, HPC, polyvinyl alcohol, polyethylene glycol or the like. Suitable examples of the aqueous suspension of the coating agent include an aqueous suspension of ethyl cellulose (EC), acrylic polymers, hydroxyprolylmethyl ethyl cellulose phtharate, cellulose acetate phtharate, carboxymethyl cellulose, cellulose acetate, hydroxypropylmethyl cellulose acetate succinate, shellac, silicone polymer or the like. As commercially available products, for example, TC-5 (HPMC; Shinetsu Kagaku), EC-N-10F (EC; Shinetsu Kagaku), Aquacoat (an aqueous suspension of EC; FMC, US), Eudragit L30D-55 or Eudragit 30D (an aqueous suspension of acrylic polymer; Röhm Pharma, WG), or the like can be used. These coating agents can be used alone or in a combination of two or more of the coating agents listed above. An aqueous solution or suspension of a coating agent can contain a water soluble substance for controlling the dissolution rate, plasticizer, stabilizer, colorant, chemical substance, or the like. The amount of the coating depends on the purpose thereof and a nature of the coating, but usually is 2 to 30% by weight of the elementary granules.

The resulting spherical granules optionally can be further coated with a powder layer comprising a pharmacologically active ingredient and a layer of a coating agent.

The spherical granules thus prepared can be filled in capsules by a conventional procedure, or after being mixed with a suitable excipient, can be compressed to form tablets.

EXAMPLES

The present invention will now be further illustrated by, but is by no means limited to, the following examples. In the Examples, the methods of evaluation of the microcrystalline cellulose, spherical seed cores, and spherical granules are as follows. Microcrystalline cellulose having a crystallinity of at least 10% is used throughout the examples. In the examples and throughout the specification and claims, all parts and percentages are by weigh unless otherwise specified.

Crystalline cellulose

The average degree of polymerization was determined by a cuprammoniom solvent method described in Industrial and Engineering Chemistry, Vol. 42, p 502 (1950).

The water absorption capacity (ml/g) was determined by a method for measuring oil absorption, as described in JIS (Japan Industrial Standard) K5101, except that distilled water was used in place of oil. The end point is the point at which water started to separate from the mass after the whole became a mass.

The fractions on 200 meth-sieve (%) was determined using a Ro-Tap sieve shaker (Yanagimoto) and sieving 30 g of a sample through a 75 μm opening (200 mesh) JIS sieve for 30 minutes, and thereafter measuring the amount of residual material.

Spherical seed cores

The water absorption capacity (ml/g) was determined by adding 30 ml of water to 10 g (as drying content) of spherical seed cores; allowing the mixture to stand at a room temperature for one hour, filtering the solid, removing surface-adsorbed water with filter paper, weighing the solid, and dividing the water content by 10. The tests were repeated five times, and an average value was obtained therefrom.

The average particle size (μm) was determined using Ro-Tap sieve shaker (Yanagimoto) and sieving 30 g of a sample through JIS sieves for 10 minutes, and a particle size at a cumulative 50% by weight was taken as the average particle size.

The aspect ratio was determined by taking a photograph of granules, calculating a ratio of the length of the short axis/the length of the long axis for 100 granules, and obtaining an average value therefrom.

The tapped bulk density (g/ml) was determined by filling 30 g of a sample in a 100 ml graduated cylinder, tapping it about 30 times, and reading the volume of the content. The test was repeated three times, and an average value thereof obtained.

The friability (%) was determined by introducing 10 g of a sample into a friabilator, rotating the sample at 25 rpm for 15 minutes, and measuring the weight loss due to abrasion. The test was repeated three times and an average value thereof obtained.

Spherical granules

The yield (%) was determined by dividing the total amount of obtained spherical granules by the total amount of materials used.

The degree of aggregation (%) was determined by dispersing spherical granules on paper and observing the presence of aggregated granule masses per 1,000 granules.

The dissolution ratio of the active ingredients (%) was determined by a paddle method using an automatic dissolution test machine DT-600 (Toyama Sangyo, Japan). The test was carried out using simulated gastric fluid Japanese Pharmacopeia (JP) for 2 hours, and then simulated intestinal fluid in JP. The test was repeated three times and an average value thereof was obtained.

Example 1

First, 1.5 kg of the microcrystalline cellulose (a) shown in Table 1, having a crystallity of 65% was placed in a high speed mixing granulator (FS-10; Fukae Kogyo, Japan), 1.5 kg of distilled water was poured thereon, and the mixture was kneaded for 5 minutes. Then, 1.0 kg of the resulting wet granules were transferred to a Marumeryzer Q-230 (Fuji Powder, Japan), whose plate was rotating at 500 rpm for 10 minutes to form spheres. Simultaneously, 200 g of distilled water was fed thereto at a rate of 20 g/min. Thereafter, the spheres were allowed to stand at 40° C. for one day, dried, and sieved through a 16 mesh-sieve (opening: 1 mm) to obtain spherical seed cores (A). The properties of the spherical seed cores (A) thus obtained are shown in Table 2.

Example 2

The same procedure as described in Example 1 was repeated, except that the microcrystalline cellulose (b) shown in Table 1 was used, and a smaller amount of distilled water was added, to obtain spherical seed cores (B). The properties of the spherical seed cores (B) thus obtained are shown in Table 2.

Example 3

The same procedure as described in Example 1 was repeated, except that the microcrystalline cellulose (c) shown in Table 1 was used, and an increased amount of distilled water was added to obtain spherical seed cores (C). The properties of the spherical seed cores (C) thus obtained are shown in Table 2.

Comparative Example 1

The same procedure as described in Example 1 was repeated, except that the microcrystalline cellulose (d) shown in Table 1 was used, and an increased amount of water was added to obtain spherical seed cores (D). The properties of the spherical seed cores (D) thus obtained are shown in Table 2.

Comparative Example 2

The same procedure as described in Example 1 was repeated, except that the microcrystalline cellulose (e) shown in Table 1 was used, and a decreased amount of water was added to obtain spherical seed cores (E). The properties of the spherical seed cores (E) thus obtained are shown in Table 2.

Example 4

400 g of the spherical seed cores obtained in Example 1 were put into a centrifugal fluidized coating machine (CF-360; Freund Sangyo, Japan), and while 200 ml of an HPC (low viscosity type) aqueous solution (3% w/v) was sprayed thereon at 10 ml/min, at an air temperature of 40° C., and a rotation rate of 160 rpm, the following powder composition was fed at 30 g/min to coat the seed cores with the powder. Next, the air temperature was increased to 80° C., and the granules were dried for 30 minutes. Then the dried granules were sieved through a sieve having an opening of 100 μm to eliminate fine powder and obtain elementary granules.

| Powder composition | |
| --- | --- |
| Theophylline (Wako Pure Chemicals) | 240 g |
| Sucrose (Kyosho Seito) | 180 g |
| Corn starch (Nichi Den Kagaku) | 180 g |

Next, the elementary granules were placed in a CF-360 apparatus, and the following aqueous suspension was sprayed at 40 ml/minute, at an air temperature of 80° C. and a rotation rate of 200 rpm, to form a coating for a sustained release.

| Composition of aqueous suspension | |
| --- | --- |
| Aquacoat (EC aqueous dispersion; 30% w/v; FMC, US) | 400 g |
| Myvacet 9-40 (acetylated Monoglyceride, Koyo Shokai) | 30 g |

After coating, the granules were dried at 80° C. for one hour in a dryer, to obtain spherical granules. The degree of aggregation (%) and the yield (%) of the resulting spherical granules are shown in Table 3.

Example 5

The same procedure as described in Example 4 was repeated, except that the spherical seed cores (B) prepared in Example 2 were used to obtain spherical granules. The degree of aggregation (%) and the yield of the resulting spherical granules are shown in Table 3.

Example 6

The same procedure as described in Example 4 was repeated, except that the spherical seed cores (C) prepared in Example 3 were used to obtain spherical granules. The degree of aggregation and the yield of the resulting granules are shown in Table 3.

Comparative Example 3

The same procedure as described in Example 4 was repeated, except that the spherical seed cores (D) prepared in Comparative Example 1 were used to form spherical granules. The degree of aggregation and the yield of the resulting granules are shown in Table 3.

Comparative Example 4

The same procedure as described in Example 4 was repeated, except that the spherical seed cores (E) prepared in Comparative Example 2 were used to prepare spherical granules. The degree of aggregation and the yield of the resulting granules are shown in Table 3.

Example 7

The same procedure as described in Example 1 was repeated, except that the recipe (g) in Table 4 was used, and a smaller amount of water was added to obtain spherical seed cores (G). The properties of the resulting spherical seed cores (G) are shown in Table 5.

Example 8

The same procedure as described in Example 1 was repeated, except that the recipe (h) in Table 4 was used, and a smaller amount of water was added to obtain spherical seed cores (H). The properties of the resulting spherical seed cores (H) are shown in Table 5.

Example 9

The same procedure as described in Example 1 was repeated, except that the recipe (i) in Table 4 was used, and a smaller amount of water was added to obtain spherical seed cores (I). The properties of the spherical seed cores (I) are shown in Table 5.

Comparative Example 5

The same procedure as described in Example 9 was repeated, except that the recipe (j) in Table 4 was used, and a smaller amount of water was added to obtain spherical seed cores (J). The properties of the resulting spherical seed cores (J) are shown in Table 5.

Comparative Example 6

Nonpareil-101 (trade name; commercially available from Freund Sangyo, Japan) 42 to 32 mesh was used as the spherical seed cores (K). The properties of the spherical seed cores (K) are shown in Table 5.

Comparative Example 7

Nonpareil-103 (trade name; commercially available from Freund Sangyo, Japan) 42 to 32 mesh was used as the spherical seed cores (L). The properties of the spherical seed cores (L) are shown in Table 5.

Examples 10 to 12

The same procedure as described in Example 4 was repeated, except that the spherical seed cores (G), (H), and (I) shown in Table 5 were used to obtain spherical granules. The degree of aggregation and the yield of the resulting spherical granules are shown in Table 6.

Comparative Examples 8 to 10

The same procedure as described in Example 4 was repeated, except that the spherical seed cores (J), (K), and (L) were used to obtain spherical granules. The degree of aggregation and the yield of the resulting spherical granules are shown in Table 6.

Example 13

First, 300 g of the spherical seed cores (A) shown in Table 2 were placed in a fluidized bed coating machine (UNI GLATT, Ohkawara Kakoki), and while fluidizing the spherical seed cores at an inlet air temperature of 60° C., 600 ml of a 20% w/v aqueous solution of L-ascorbic acid (Wako Pure Chemicals) was sprayed thereon at 10 ml/min, to coat the spherical seed cores with L-ascorbic acid. The L-ascorbic acid-coated granules were fluidized for 5 minutes, until dry, to obtain elementary granules. Next, as a moisture-proof coating, 150 ml of a 10% w/v aqueous solution of TC-5 (HPMC; Shinetsu Kagaku) was sprayed at 10 ml/min, and fluidized for 20 minutes until dry. Thereafter, the granules were sieved through a sieve having an opening 100 μm, to eliminate fine powder and obtain spherical. granules. The degree of aggregation and the yield of the resulting spherical granules are shown in Table 7.

Comparative Example 11

The same procedure as described in Example 13 was repeated, except that the spherical seed cores (K) shown in Table 5 were used to obtain spherical granules. The degree of aggregation and the yield are shown in Table 7.

Example 14

First, 400 g of the spherical seed cores (G) shown in Table 5 were placed in a centrifugal-fluidized coating machine (CF-36; Fleund Sangyo, Japan), and while 70 ml of a 6% w/v aqueous solution of polyvinyl pyrrolidone (K-30; BASF) was sprayed at 70 ml/minute, at an air temperature of 40° C. and a rotation rate of 160 rpm, the following powder composition was fed at 8 g/min to coat the seed cores with the powder. Thereafter, the air temperature was increased to 60° C., and the powder-coated granules were dried for 20 minutes. Next, the resulting granules were sieved through a sieve having an opening of 100 μm, to eliminate fine powder and obtain elementary granules.

| Powder composition | |
|---|---|
| Chlorophenylamine maleate (Wako Pure Chemicals) | 50 g |
| Corn starch | 30 g |

Next, the elementary granules were placed in a fluidized bed coating machine (UNI GLATT; Ohkawara Kakoki). While fluidizing the elementary granules at an inlet air temperature of 60° C., an aqueous suspension was sprayed onto the granules at 20 ml/min, to coat the granules.

| Composition of aqueous suspension | |
|---|---|
| Eudragit L-30D-55 (Löhm Pharma, WG) (30% w/v) | 200 g |
| Talc (Wako Pure Chemicals) | 10 g |
| Triethyl citrate (Wako Pure Chemicals) | 6 g |
| Distilled water | 184 g |

After the coating operation, the granules were dried at 40° C. for 16 hours to obtain enteric spherical granules. The degree of aggregation and the yield of the enteric spherical granules are shown in Table 8.

Comparative Example 12

The same procedure as described in Example 14 was repeated, except that the spherical seed cores (K) shown in Table 5 were used to obtain spherical granules. The aggregation degree and coating ratio of the resulting spherical granules are shown in Table 8.

A comparison of the dissolution rate of the active ingredient from the spherical granules of Example 4 and of the spherical granules of Example 11 is shown in FIG. 1.

TABLE 1

| | Microcrystalline cellulose (MCC) | | | | |
|---|---|---|---|---|---|
| | (a) | (b) | (c) | (d) | (e) |
| Water absorption capacity (ml/g) | 2.1 | 1.5 | 2.6 | 3.0 | 0.8 |
| Fractions on 200 mesh-sieve (%) | 30 | 15 | 25 | 48 | 5 |
| Average degree of | 220 | 140 | 320 | 390 | 40 |

TABLE 1-continued

| | Microcrystalline cellulose (MCC) | | | | |
|---|---|---|---|---|---|
| | (a) | (b) | (c) | (d) | (e) |
| polymerization | | | | | |

TABLE 2

| | Spherical seed cores | Water absorption capacity (ml/g) | Average particle size (μm) | Aspect ratio | Tapped bulk density (g/ml) | Friability (%) |
|---|---|---|---|---|---|---|
| Exam. 1 | (A) | 1.00 | 380 | 0.91 | 0.93 | 0.0 |
| Exam. 2 | (B) | 0.75 | 350 | 0.90 | 0.98 | 0.1 |
| Exam. 3 | (C) | 1.40 | 450 | 0.75 | 0.80 | 0.0 |
| Comp. Exam. 1 | (D) | 1.70 | 420 | 0.65 | 0.60 | 0.0 |
| Comp. Exam. 2 | (E) | 0.40 | 300 | 0.85 | 0.90 | 1.5 |

TABLE 3

| | Degree of aggregation (%) | Yield (%) |
|---|---|---|
| Example 4 | 0.5 | 99.8 |
| Example 5 | 0.8 | 99.6 |
| Example 6 | 0.3 | 98.8 |
| Comparative Example 3 | 1.5 | 96.5 |
| Comparative Example 4 | 3.6 | 97.7 |

TABLE 4

| Recipe | MCC (a) | Lactose | CS | Sucrose |
|---|---|---|---|---|
| (g) | 100 | — | — | — |
| (h) | 90 | 5 | 5 | — |
| (i) | 70 | 15 | 15 | — |
| (j) | 30 | 35 | 35 | — |
| (k) | — | — | 25 | 75 |
| (l) | — | — | — | 100 |

(% by weight)

TABLE 5

| | Spherical seed cores | Water absorption capacity (ml/g) | Average particle size (μm) | Aspect ratio | Tapped bulk density (g/ml) | Friability (%) |
|---|---|---|---|---|---|---|
| Exam. 7 | (G) | 1.10 | 220 | 0.90 | 0.91 | 0.0 |
| Exam. 8 | (H) | 0.95 | 300 | 0.88 | 0.90 | 0.0 |
| Exam. 9 | (I) | 0.75 | 550 | 0.83 | 0.80 | 0.5 |
| Comp. Exam. 5 | (J) | disintegrated | 300 | 0.80 | 0.72 | 1.2 |
| Comp. Exam. 6 | (K) | dissolved | 380 | 0.90 | 0.85 | 4.8 |
| Comp. Exam. 7 | (L) | dissolved | 400 | 0.90 | 0.97 | 2.2 |

TABLE 6

| | Degree of aggregation (%) | Yield (%) |
|---|---|---|
| Example 10 | 0.9 | 99.2 |
| Example 11 | 0.8 | 99.0 |
| Example 12 | 1.1 | 99.0 |
| Comparative Example 8 | 3.3 | 97.2 |
| Comparative Example 9 | 6.2 | 95.4 |
| Comparative Example 10 | 10.8 | 96.6 |

TABLE 7

| | Degree of aggregation (%) | Yield (%) |
|---|---|---|
| Example 13 | 1.1 | 99.3 |
| Comparative Example 11 | 7.9 | 94.4 |

TABLE 8

| | Degree of aggregation (%) | Yield (%) |
|---|---|---|
| Example 14 | 1.4 | 99.0 |
| Comparative Example 12 | 7.2 | 95.5 |

In a process for the production of spherical granules wherein seed cores are coated with powder containing a pharmacologically active ingredient, an aqueous solution or suspension of a coating agent is sprayed thereon and the coated granules are dried to form spherical granules, by using spherical seed cores having a high water absorption capacity and a low friability, as defined in the present invention, there are obtained commercially valuable spherical granules wherein the aggregation is reduced to one tenth of that of granules using conventional seed cores such as Nonpareil and the yield is increased by 5% compared with granules using conventional seed cores.

Moreover, since the granules of the invention comprise spherical seed cores which are dissolved with difficulty in a gastric and enteric environment, the pharmacologically active ingredients are dissoluted at a constant rate for a long time as shown in FIG. 1. Furthermore, the present spherical seed cores are not substantially disintegrated in water and have a high strength. Thus, upon administration in vivo, the spherical granules are only slightly disintegrated by intestinal movement and provide a desirable dissolution profile.

It will be apparent to those skilled in the art that various modifications and variations can be made in the present invention without departing from the scope or spirit of the invention. Thus, it is intended that the present invention cover the modifications and variations of this invention provided they come within the scope of the appended claims and their equivalents.

What is claimed is:

1. A process for the production of a spherical granule, comprising the steps of:

(1) coating a spherical pharmacologically inactive seed core which comprises at least 50% by weight of microcrystalline cellulose with a powder comprising a pharmacologically active ingredient by
  (a) simultaneously spraying the powder comprising the pharmacologically active ingredient and an aqueous binding solution onto the spherical pharmacologically inactive seed core, or
  (b) spraying an aqueous binding solution or suspension into which the powder comprising the pharmacologically active ingredient is dissolved or suspended onto the spherical pharmacologically inactive seed core,
to form said spherical seed core coated with a powdery layer, wherein said microcrystalline cellulose has an average degree of polymerization of 60 to 375, and said spherical pharmacologically inactive seed core has an average particle size of 100 to 1000 μm, a tapped bulk density of at least 0.65 g/ml, an aspect ratio of at least 0.7, a water absorption capacity of 0.5 to 1.5 mg/g, and a friability of no more than 1%;
(2) spraying an aqueous solution or suspension of a coating agent onto said spherical seed core coated with the powdery layer to form a coated granule; and
(3) drying the coated granule to form said spherical granule.

2. A process according to claim 1, wherein said spherical granule comprises 5 to 300% by weight of said powder relative to the weight of said spherical pharmacologically inactive seed core.

3. A process according to claim 1, wherein said aqueous binding solution or suspension in step (1) comprises a binding agent selected from the group consisting of hydroxypropyl cellulose, hydroxypropyl methyl cellulose, methyl cellulose, starch paste, pregelatinized starch, polyvinyl pyrrolidone, gum arabic, sugar syrup and sodium carboxymethyl cellulose.

4. A process according to claim 1, wherein said powdery layer further comprises an excipient selected from the group consisting of lactose, corn starch, microcrystalline cellulose, sucrose, D-mannitol, and pregelatinized starch.

5. A process according to claim 1, wherein said coating agent is selected from the group consisting of ethyl cellulose, acrylic polymers, hydroxypropylmethyl ethyl cellulose phthalate, cellulose acetate phthalate, carboxymethyl cellulose, cellulose acetate, hydroxypropylmethyl cellulose acetate succinate, shellac and a silicone polymer.

\* \* \* \* \*